US00PP27880P2

(12) United States Plant Patent
Hansen

(10) Patent No.: US PP27,880 P2
(45) Date of Patent: Apr. 11, 2017

(54) ***HIBISCUS* PLANT NAMED 'PERFECT STORM'**

(50) Latin Name: ***Hibiscus* hybrid (L.)**
Varietal Denomination: Perfect Storm

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 7 days.

(21) Appl. No.: 14/757,106

(22) Filed: Nov. 19, 2015

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Susan McCormick Ewoldt

(57) ABSTRACT

A new and distinct cultivar of winter-hardy, herbaceous, perennial, hybrid *Hibiscus* plant named 'Perfect Storm' comprising a short compact habit of multiple, well-branched, basal stems producing numerous flowers from the ground up, over a prolonged season having light pink to near white base and bright-red eye and veins and marginal red tinting. The foliage is three to five-lobed, deeply dissected, maple-like and dark purple colored.

1 Drawing Sheet

Botanical classification: *Hibiscus* hybrid (L.).
Variety denomination: 'Perfect Storm'.

BACKGROUND AND ORIGIN OF THE PLANT

The present invention relates to the new and distinct hardy, herbaceous, *hibiscus* plant, *Hibiscus* 'Perfect Storm' hybridized by the inventor on Jul. 27, 2011 at a nursery in Zeeland, Mich. The new plant is a single seedling selection from a cross between *Hibiscus* 'Crown Jewels' U.S. Plant Pat. No. 11,857 (female seed parent) times *Hibiscus* 'Midnight Marvel' U.S. Plant Pat. No. 24,079 (male pollen parent). The seeds were harvested on Nov. 11, 2011 and the specific seedling passed the initial trial in the summer of 2013 at which time it was assigned the breeder code labeled # 11-117-6. Both parents have a complex mixture of species in them, most likely including the species: *moscheutos* and *coccineus*. *Hibiscus* 'Perfect Storm' was first asexually propagated in 2013 by sterile shoot-tip tissue culture at the same nursery in Zeeland, Mich. The resultant asexually propagated plants have been found to be stable and true to type in successive generations of asexual reproduction.

No plants have been sold, either in this country or anywhere in the world, prior to the filing of this application, nor has any disclosure been made prior to the filing of this application with the exception of that which was within one year of the filing of this application and was derived directly or indirectly from the inventor.

BRIEF SUMMARY OF THE PLANT

*Hibiscus* 'Perfect Storm' differs from its parents as well as all other hardy herbaceous *hibiscus* known to the applicant in many traits. The most similar *hibiscus* in flower color known to the applicant are *Hibiscus* 'Summer Storm' U.S. Plant Pat. No. 20,443, *Hibiscus* 'Kopper King' U.S. Plant Pat. No. 10,793 and *Hibiscus* 'Copper Queen' U.S. Plant Pat. No. 23,941. The habit of the new plant is shorter and more compact. Compared to the female parent 'Crown Jewels' the new plant has much darker purple foliage, the flowers are larger and have more red veining. Compared to the male parent 'Midnight Marvel', the new plant has flowers that are more white with red veining, and the habit is shorter and more compact. Compared to 'Summer Storm', the new plant is shorter and more compact. Compared to 'Kopper King', the new plant is darker purple and finer in leaf texture; shorter, more compact and more branched in habit; and flowers for a longer season with flowers that cover from the bottom to the top of the plant. Compared to 'Copper Queen', the new plant has darker purple foliage and the flowers are flatter faced.

*Hibiscus* 'Perfect Storm' is a unique hardy herbaceous *hibiscus* with the following combined traits:

1. Winter-hardy, perennial with short compact habit of multiple, well-branched, basal stems.
2. Many rotate, flat-faced flowers over a prolonged season being produced from the ground to the top of the plant.
3. Flower petals having very light pink to near white base, a lustrous bright-red eye zone and veins of bright-red, with marginal red tinting on the distal portion.
4. Dark-purple, deeply-dissected, three to five-lobed, maple-like foliage.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
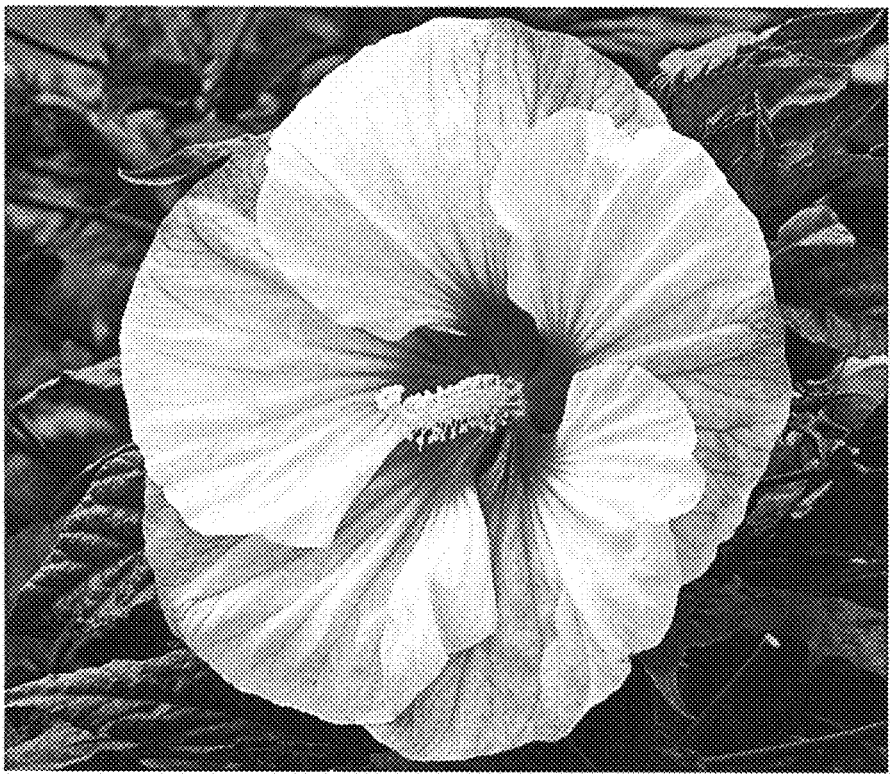
FIG. 1 shows a close-up of the flower.
Figure 2:
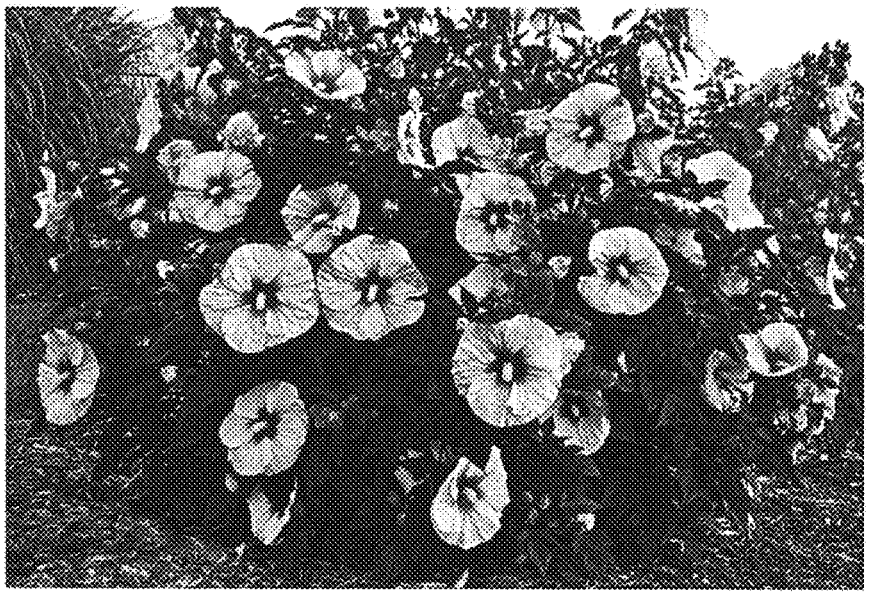
FIG. 2 shows the plant in full flower.

The following descriptions and color references are based on the 2001 edition of The Royal Horticultural Society Colour Chart except where common dictionary terms are used. The new plant, *Hibiscus* 'Perfect Storm', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand, open-field full-sun trials of a nursery in Zeeland, Mich. with supplemental fertilizer and water as needed. The plants are of natural habit and were not treated with plant growth regulators, nor were they pinched at any time in the growth year.

Parentage: *Hibiscus* 'Crown Jewels' U.S. Plant Pat. No. 11,857 (female seed parent) times *Hibiscus* 'Midnight Marvel' U.S. Plant Pat. No. 24,079 (male pollen parent).

Propagation:

*Method*.—Stem cuttings and sterile shoot-tip plant tissue culture division.

*Time to initiate roots from tissue culture*.—About two weeks.

*Rooting habit*.—Normal, branching, developing thick to about 3.0 cm diameter, fleshy; root color creamy yellow between RHS 161D and lighter than RHS 159D depending on soil type.

*Crop time*.—Under normal summer growing conditions 12 to 16 weeks to flower in a four-liter container from cutting. Plant vigor is very good.

Plant description:

*Plant habit*.—Hardy herbaceous perennial with 12 to 15 thick upright and heavily branched main stems producing a upright spreading mound to about 92.0 cm tall and about 120.0 cm wide, widest about 45 cm above soil line; 12 to 16 primary branches per main stem protruding at about 80° from horizontal for lowest branches to about 45° angle from horizontal for distal branches; flowering from base to top of plant with about 40 to 48 flowers per main stem.

*Stem*.—Terete, glabrous, glaucous; to about 90.0 cm tall and about 2.3 cm diameter at base, average about 82.0 cm tall and about 16.0 mm diameter at base.

*Stem color*.—Base between RHS 144B and RHS 144A with large patches of various lengths in high light exposed portions of between RHS 182B and RHS 183A; distal portion between RHS 183A and RHS 187C.

*Lateral branches*.—Terete, glabrous, glaucous; to about 38.0 cm long and 6.5 mm diameter.

*Lateral branch color*.—Between RHS 183A and RHS 187C.

*Internode*.—About 12 nodes per stem below flowers, average internode length about 4.0 cm of unpinched plant below flower, and average about 2.5 cm in upper flowering section without branches, largest in middle portion of stem.

*Internode color*.—Varying with light exposure, same as surrounding stem.

Foliage description: Alternate; dentate; glabrous; deeply cleft, mostly three-lobed with some five-lobed; lustrous adaxial center, dull adaxial sides and below; leave blades to about 16.0 cm long and about 16.0 cm across, leaf blade size average 15.0 cm long and 13.0 cm wide, becoming smaller distally; no fragrance detected.

*Foliage color*.—Adaxial between RHS N186A and RHS N186B with a green base of nearest RHS 139B sometimes showing; abaxial between RHS 147B and RHS N138C.

*Veins*.—Palmate; lustrous; ridged on abaxial.

*Vein color*.—Adaxial proximally nearest RHS 187B becoming RHS N186C and progressing to nearest RHS N186B distally; abaxial between RHS 187C and RHS 185B proximally and becoming nearest RHS 185C toward leaf margins.

*Petioles*.—Mostly terete, slightly flattened at base; glaucous; glabrous; to about 8.0 cm long and 5.0 mm diameter at base, average size about 6.5 cm long and 4.0 mm wide.

*Petiole color*.—Adaxial between RHS 187B and RHS 187C; abaxial between RHS 184B and RHS 183C.

Flower description: Complete; actinomophic; upward to outward facing; rotate; lasting about two days on plant; no fragrance detected.

*Buds one day prior to opening*.—Ovoid with rounded apex and bluntly rounded base; carinate at sepal fusions; unopened petals wrinkled at veins; about 6.4 cm long and about 4.3 cm across.

*Bud color*.—Exposed petal color just above sepals nearest RHS N155C, distal petal portion and veins between RHS 58A and RHS 60C; color of sepal base nearest RHS 144A and with tinting in the distal portion to nearest 185B.

*Epicalyx*.—Entire, glabrous, dull surface abaxial and adaxial; linear with sharply acute apex and attenuate base, arcuate upwards near calyx; typically 10 to 12 per flower; about 2.5 cm long tapering to base of about 3.0 mm wide; adaxial and abaxial color between RHS 141C and RHS 143C with abaxial tinting of nearest RHS 183C.

*Sepals*.—Five; glabrous, slightly glaucous abaxial; acute apex; margin entire, edentate; abaxial and adaxial surfaces matte; fused in base; about 3.6 cm long, fused in about the basal 2.2 cm, about 2.4 cm wide at fusion, proximal 1.4 cm connate forming campanulate star-shaped calyx.

*Sepal color*.—Abaxial base between RHS 144A and RHS 143C with distal tinting nearest RHS 183C; adaxial color between RHS 145B and RHS 145C.

*Flowers*.—Solitary, about 40 to 45 per main stem without pinching; slightly cupped petals and lightly pleated at veins giving extra strength to resist high winds; upward and outwardly facing; average 19.0 cm across and 6.8 cm deep from outside face to edge of reflexed petals, larger in early part of flowering season; persist for a one to two days; effective for at least 9 weeks beginning early August and lasting into October; no detectable fragrance.

*Petals*.—Five; glabrous, slightly lustrous in center and dull both front and back toward middle and perimeter; adnate to the androecium to form a column, imbricate to about 100% overlapping at widest part (petals overlapping completely to the petals on either side), palmately veined, primary and secondary veins impressed on front and ribbed on back; shape: rounded with distinct claw and limb; margins: entire, edentate; apex: rounded; base: short claw-like; size: average about 9.0 cm long and about 13.0 cm wide at widest portion (larger in earlier part of flowering season); center dark eye about 6.5 cm diameter.

*Petal color*.—Adaxial center nearest RHS N155C, apex distal overlapped portion blushed with nearest RHS 60C, veins extending from eye between RHS 60B and RHS 60C lightening to nearest RHS N155C distally, eye nearest RHS 53B in outer about 5.0 mm and proximally nearest RHS 53C; abaxial color between RHS 70B and RHS 70C with exposed eye between RHS 61C and RHS 61B; adaxial central portion between eye and margin lighter than RHS N155D or RHS N155C, apex and veins radiating from apex between RHS 60B and RHS 60C.

*Gynoecium*.—Single; partially enclosed in column. Column: glabrous, lustrous; about 5.5 cm long and about 1.2 cm wide at base; Column color: basal 1.0 cm between RHS 61C and RHS 61D, distal 4.5 cm whiter and lighter than RHS 155D; Style: split in distal about 7.0 mm portion into typically five branches and protruding from column, branch diameter about 1.5 mm; branch color nearest RHS N155C; Stigma: typically five; globose, puberulent, about 3.0 mm in diameter; color nearest RHS 159D; Ovary: superior, about 8.5 mm across at base and about 8.0 mm tall; acute apex; color between RHS 145B and RHS 145C;

*Androecium*.—Filaments: numerous, about 160; less than about 1.0 mm in diameter and about 5.0 mm long; attached along nearly the entire length of column; color nearest RHS N155C; Anthers: reniform; dorsifixed; about 2 mm long and 1 mm wide; color nearest RHS 155A; Pollen: numerous, globose, less than 0.1 mm long; color nearest RHS 155D.

*Pedicel*.—Terete, glabrous, glaucous; length from base of sepal to abscission point about 14.0 cm long and about 2.5 mm wide, longer on early flowers and decreasing in distal flowers; color nearest RHS 138B with tinting of nearest RHS 184B in more intense light.

*Peduncle*.—Terete, glabrous, glaucous; about 4.5 cm long from abscission point to stem and about 3.5 mm wide at base, shorter on upper flowers; color nearest RHS 185A.

*Fruit*.—Loculicidal capsule; puberulent; globose, with abruptly acute apex; color variable between RHS N199B and RHS N199C when mature.

*Seed*.—Minutely floccose, typically globose; about 3.0 mm in diameter; color between RHS 165B and RHS N199B.

Resistance: The flowers of 'Perfect Storm' have resisted wind, rain and hot sun conditions better than typical hardy perennial *hibiscus*. Other pest and disease resistance beyond that of other hardy perennial *hibiscus* cultivars has not been observed. The plant grows best with plenty of moisture, but is able to tolerate some drought once established. Hardiness at least from USDA zone 4 through 9, and other disease resistance is typical of that of other hardy *hibiscus* cultivars.

I claim:

1. A new cultivar of hardy herbaceous perennial *Hibiscus* hybrid plant named 'Perfect Storm' as herein illustrated and described, suitable for potted plant culture, landscaping as a specimen or en masse, and especially suited for patios and confined spaces because of the short compact habit.

* * * * *